United States Patent [19]

Gwyn

[11] Patent Number: 4,459,992

[45] Date of Patent: Jul. 17, 1984

[54] ARTERIAL PULSE RATE MONITOR AND STRESS WARNING DEVICE

[76] Inventor: Marion V. Gwyn, 8035 Coolidge, Centerline, Mich. 48015

[21] Appl. No.: 441,473

[22] Filed: Nov. 15, 1982

[51] Int. Cl.³ .............................................. A61B 5/02
[52] U.S. Cl. ...................................... 128/687; 128/698
[58] Field of Search ................................ 128/687–690, 128/701; 73/DIG. 1; 340/573, 683; 200/61.45 R, 61.48, 61.51

[56] References Cited

U.S. PATENT DOCUMENTS

| | | | |
|---|---|---|---|
| 2,974,521 | 3/1961 | Phelps | 200/61.48 |
| 3,535,067 | 10/1970 | Lesher et al. | 128/690 |
| 3,841,315 | 10/1974 | Kopp | 128/701 |
| 3,861,387 | 1/1975 | Lawhorn et al. | 128/701 |
| 3,899,649 | 8/1975 | Jenkins | 200/61.51 |
| 4,158,962 | 6/1979 | Conoval | 73/DIG. 1 |
| 4,262,674 | 4/1981 | Uemura et al. | 128/689 |

FOREIGN PATENT DOCUMENTS 2922542 12/1980 Fed. Rep. of Germany ...... 128/689

Primary Examiner—William E. Kamm
Assistant Examiner—Mitchell J. Shein
Attorney, Agent, or Firm—Peter A. Taucher; John E. Becker; Robert P. Gibson

[57] ABSTRACT

A rugged, relatively low cost, reliable warning device wearable on a person's body, preferably in the form of a bracelet or wristwatch. This device novelly utilizes the principal of natural sympathetic vibration or harmonic response of a fine metal reed, such as a finely drawn tungsten wire, to effect closing of an electrical circuit which hereby emits an appropriate warning signal or combination of signals. The device further embodies adjustable frequency of response calibration selection in combination with the selective electrical circuit features to promptly detect an excessive heartbeat or pulse rate. The signal emitted may be of audio, visual or sensory form or a combination thereof to warn the user against over exertion, stressful situations.

This device is unlike known prior art devices of the strain gauge and piezo-electric types, which rely upon electrical circuit resistance changes, as well as other types of the electromagnetic and pressure transducer types which use electrical circuit impulses to sense pulse rates.

12 Claims, 19 Drawing Figures

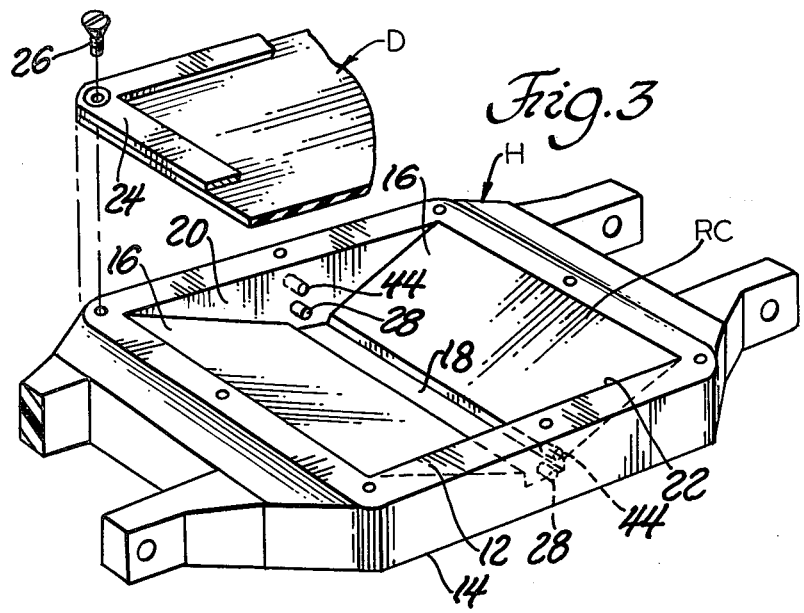

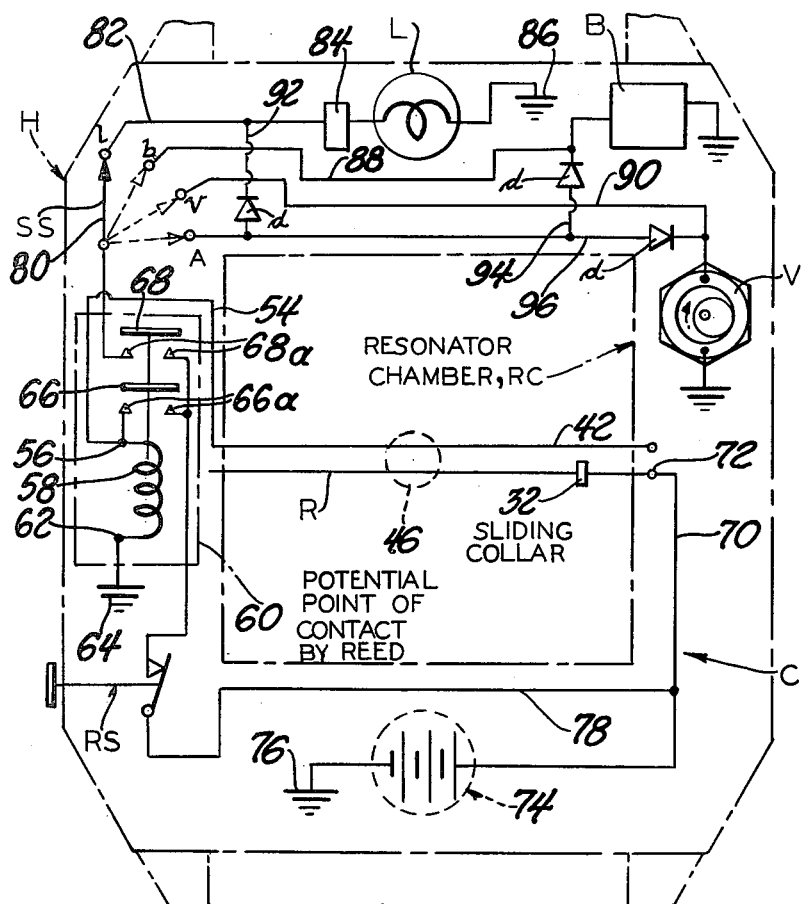
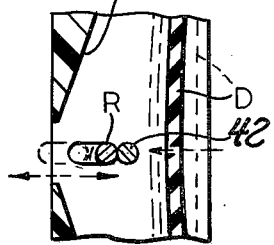
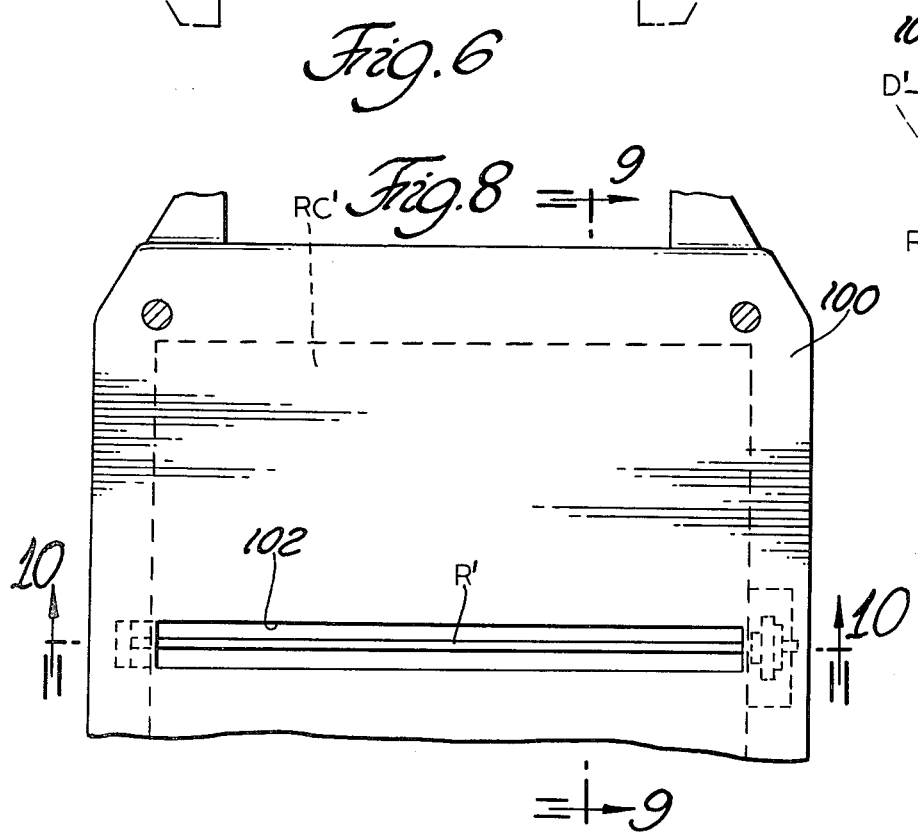
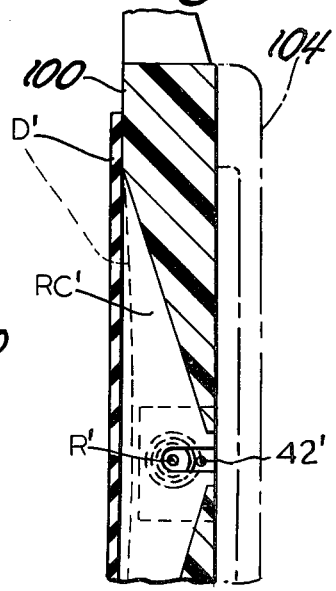

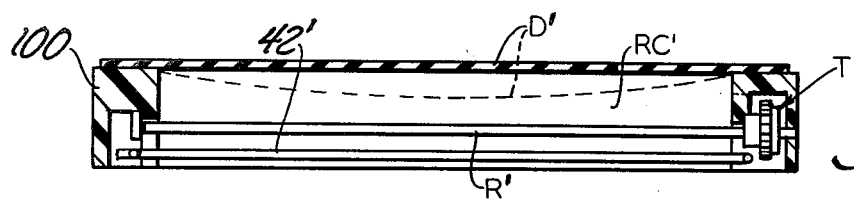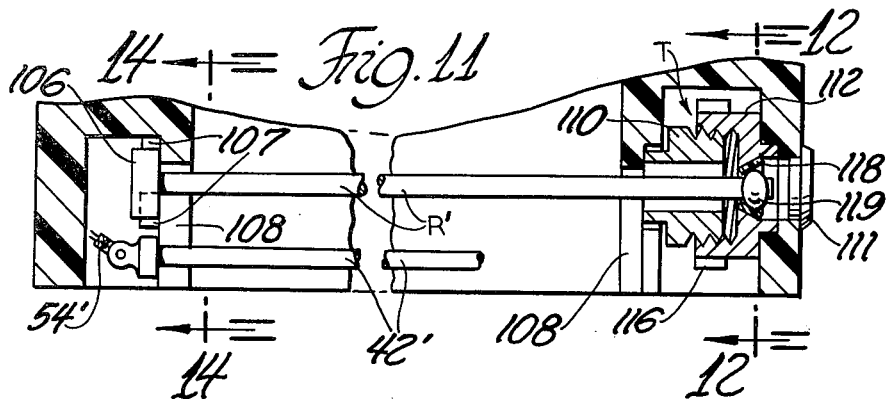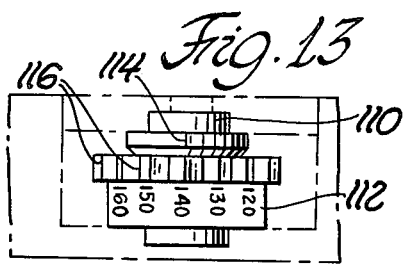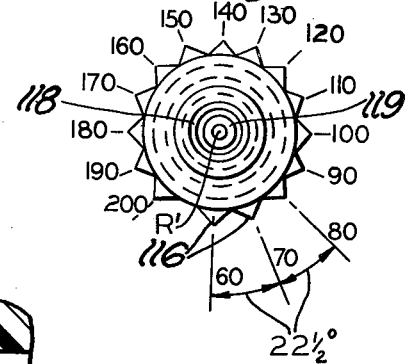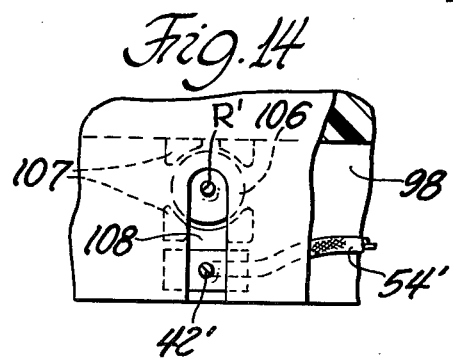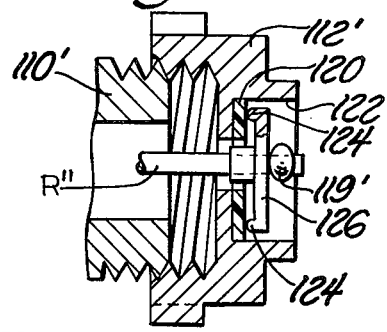

ARTERIAL PULSE RATE MONITOR AND STRESS WARNING DEVICE

GOVERNMENT INTEREST

The invention described herein may be manufactured, used, and licensed by or for the Government for governmental purposes without payment to me of any royalty thereon.

BACKGROUND AND OBJECTS OF THE INVENTION

The present invention relates generally to a physical stress warning device for detecting and warning of excessive heartbeat via monitoring of an arterial pulse rate. More specifically, it relates primarily to such a device having novelly improved construction, and more preferably being of the bracelet or wristwatch style which is of relatively simple, rugged construction providing a high degree of reliability.

Various generally similar prior art devices have been proposed and/or heretofore used. However, unlike my invention, mostly they have been either of the piezo electric and strain gauge types using circuitry and read-out devices responsive to elecrical circuit resistance changes, or they have been of the electromagnetic and pressure transducer types relying upon electrical circuit impulses to sense and record respective pulse rates being monitored.

Numerous persons are troubled by various cardiac heart problems. Heartbeat rates of approximately 72 beats per minute have been considered to be normal (ref. Encyclopedia Britannica, 1960 Edition). Various factors including illness, disease, tension, emotional and physical exercising all contribute to commonly increase the heartbeat rate quite frequently to between 100 and 120, or greater and which rates may initiate strokes or heart attacks. Many find it advantageous to monitor their heartbeat in some suitable form. While some may find it desirable to have actual time and rate read out data displayed, for others it would suffice to have a monitor device calibratable to a predetermined elevated pulse rate level which upon attaining same will timely omit a warning signal of audio, visual or sensory character, or various combinations thereof.

Accordingly, it is a principal object of the present invention to provide novel, simplified portable monitor means of the latter-described character to prevent persons with heart or high blood pressure problems from exceeding safe exertional or stress limits, thereby reducing the possibility of heart attack, stroke or physical incapacition from excessive heart strain.

Another object is to evolve the sensing-warning device of the aforesaid character which is relatively inexpensive, being devoid of any associated electrical or visual quantitive measuring equipment or capability, and which device is easily attachable to and removable from the body or body member, without inconvenience or discomfort to the wearer.

BRIEF SUMMARY OF THE INVENTION

The foregoing and other objects and advantages hereof will become more evident from the hereinafter more-detailed written description. However, briefly stated, the foregoing objects are achieved by the provision of a housing case having a diaphragm-vibratable resonator reed or wire disposed at a tapered end of a shallow horn or hopper-shaped resonator-amplifier chamber. It further novelly uses the natural sympathetic vibrations of a resonator reed fabricated from a specially selected material. The reed member is the only mechanically movable part which upon vibration at proper frequency strikes electrical contact, and thereby initiates activation of a simplified associated electrical warning signal circuit embodied either integrally within the case and/or mounting straps, or in an ancillary pack readily carried on the body or in the clothing. The device is adapted to be worn with the diaphragm side overlaying a pulsating artery, such as at the underside of the wrist.

PRIOR ART DISCUSSION

None of the prior art patented devices or other devices in commercial use of which I am aware to utilize the principal or structure of my substantive novelly improved and simplified device. While some of the prior patented devices variously embody diaphragm and/or flexural beam-like members they are all substantively, structurally and functionally patentably different from the present invention. Prior art patents of general interest include U.S. Pat. Nos. 1,675,799; 1,675,800; 2,549,049; 3,154,066; 3,553,625; 3,593,704; and 3,713,341.

BRIEF DESCRIPTION OF DRAWINGS

The following detailed description of one or more preferred embodiments should be considered in conjunction with the accompanying drawings, in which:

FIG. 3 is an enlarged scale perspective view of the principal base or case member, fragmentarily showing in exploded relationship the diaphragm and its clamping ring means.

FIG. 4 is an enlarged scale plan view primarily of the reverse side of the case portion of FIG. 3, with the main cover portion shown broken away to better see the details of the adjustment means and pulse rate scale.

FIG. 5 is a cross-sectional view taken substantially on line 5—5 of FIG. 4.

FIG. 6 is a schematic of one form of electrical circuit arranged generally to fit within the device's basic housing case depicted therewith in broken lines.

FIG. 7 is a fragmentary cross-sectional detail view through the case at a point where the vibrating reed has contacted the conductor wire.

FIGS. 8 and 9 are fragmentary plan and cross-sectional views similar to FIGS. 4 and 5, but showing an alternative embodiment.

FIG. 10 is a further cross-sectional detail taken substantially on line 10—10 of FIG. 8.

FIG. 11 is a further fragmentary, cross-sectional view on an enlarged scale showing greater exemplary detail of some of the components of FIG. 10.

FIGS. 12 and 13 are end and side detail views respectively of an exemplary wire-tensioning means subassembly used in the form of FIGS. 8–11.

FIG. 14 is a further enlarged detail view taken transversely on line 14—14 of FIG. 11.

FIG. 15 is a further fragmentary longitudinal cross-sectional view similar to the right hand part of FIG. 11, through an alternative form of reed/wire fastening means in the tensioning means thereof.

FIG. 16 is a perspective view of still a further modified embodiment; and

DETAILED DESCRIPTION OF INVENTION

Figure 1:
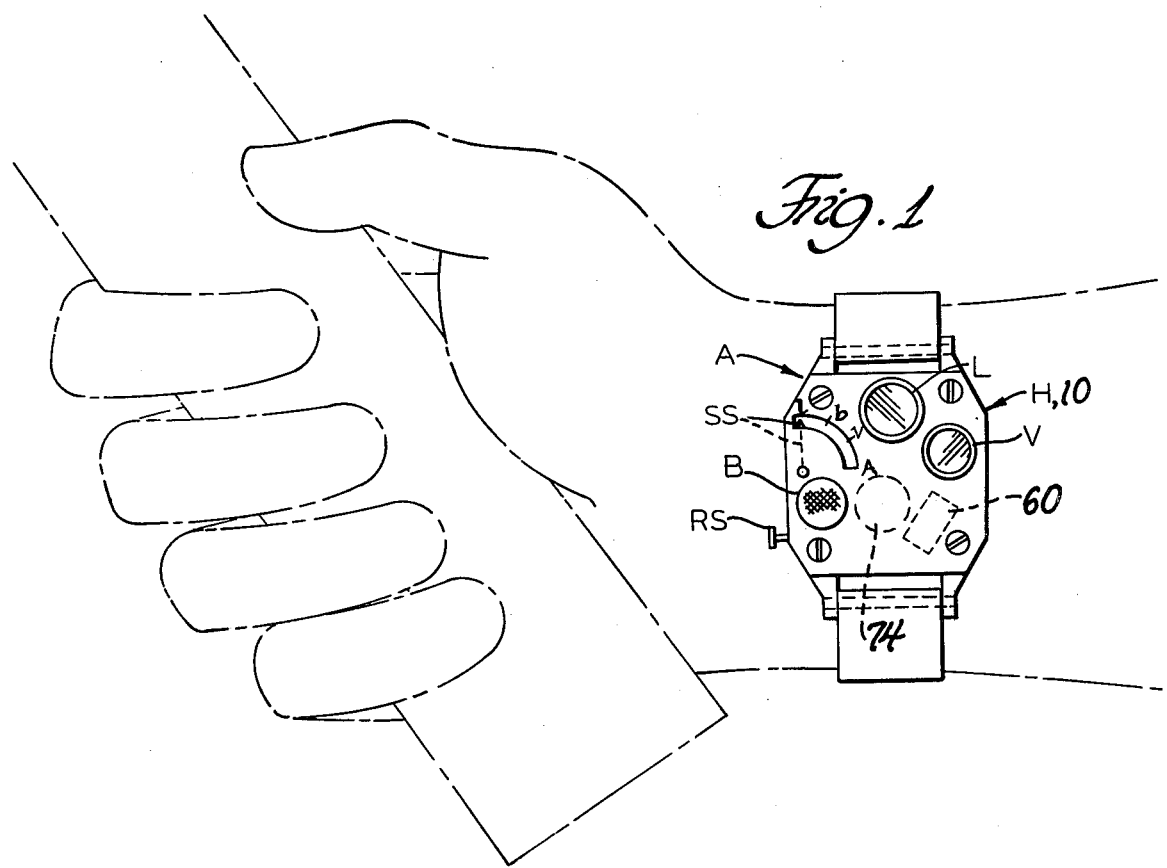
FIG. 1 is a plan view of the face side of my device shown strap attached to the wearer's wrist.
Figure 2:
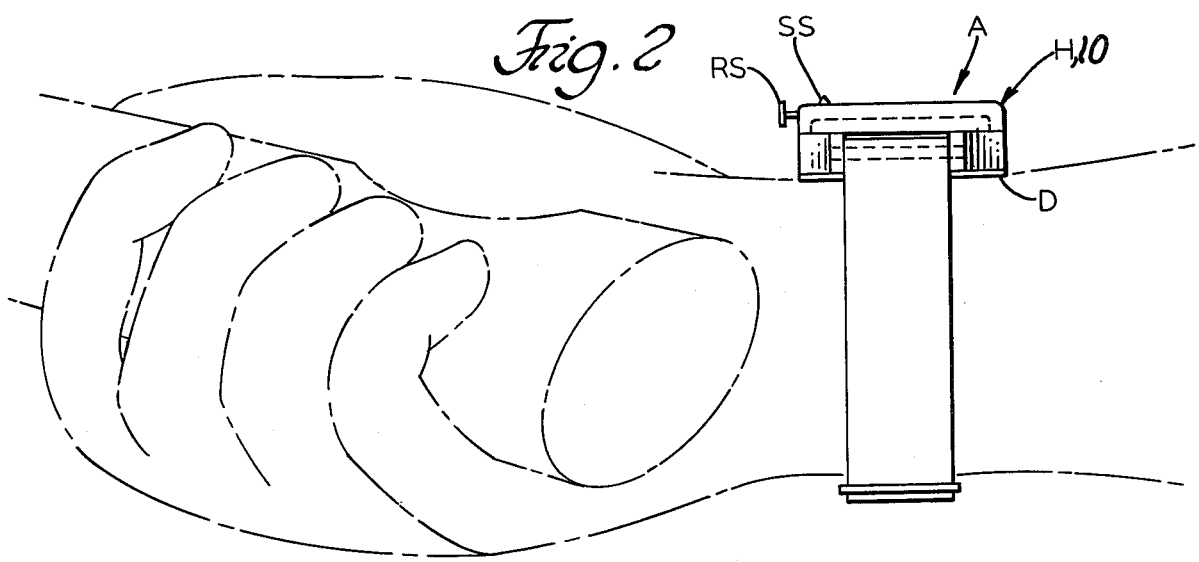
FIG. 2 is an end elevational view of the device of FIG. 1, in which the wrist and hand are shown in phantom outline.

First broadly describing one preferred form of the invention with respect to FIGS. 1-7, a warning device assembly is depicted generally as A, having a case assembly or housing body H which includes a shallow hopper-shaped or tapered horn resonator chamber RC, a resonator reed R spanning said chamber RC adjacent a narrowed slotted end, a diaphragm D overlaying the larger end of said chamber RC, and a small battery powered electrical circuit C preferably embodied essentially with case H or the associated cover part. The circuit C embodies subcircuits which can be selectively set to provide various warning signals (light L, buzzer B, vibrator V) to the wearer; and it further includes a release-reset manual switch RS.

More specifically, the assembly's main housing body is designated 10, and as shown is of generally flattened rectangular shape. Body 10 preferably has flat, parallel opposed surfaces 12, 14 and is suitably formed with at least two opposed, shallow sloping walls 16, 16 which terminate at or adjacent to the flat surface 14 in a spaced apart manner to define the elongated medial slot 18. The sloping walls 16, 16, together with opposed end walls 20, 22 collectively act to define the aforesaid shallow, hopper-shaped combined resonator and pulse amplifier chamber RC. While the ends walls 20, 22 are shown essentially parallel, it is understood that they also could be similarly inclined toward each other but preferably to a much lesser degree than walls 16, 16, so as to still define a tapered chamber or horn having an elongated slot rather than only a smaller circular or square opening.

As viewed in FIG. 3, the upper edges of walls 16, 16, and 20, 22 are coplanar with surface 12 and define the generally square larger opening which is covered by the diaphragm D. Diaphragm D is a very thin pliable membrane of rubber or plastic like material which may be applied either adhesively and/or by a generally square flattened ring shaped hold-down member 24. A plurability of tiny screw fasteners 26 mate with suitable apertures provided in membrane D, in member 24, and with mating recesses the case or housing H.

However, prior to affixing the diaphragm, a selected resonator reed must be installed. My invention utilizes the basic principal of the natural sympathetic harmonic response in a reed of a selected material, in accordance with the following universally applicable formula, to form an electrical switch:

$$f = \frac{n}{2L}\sqrt{\frac{T}{d}}$$

wherein:
  f = the characteristic or natural frequency of the reed.
  n = any whole integer, n = 1 being chosen to obtain the harmonic response range required for the design of this invention.
  L = length of vibrating reed.
  T = tension applied to reed.
  d = line density of the reed = mass per unit length.

A most practical form is deemed to be a fine diameter tungsten wire. This wire reed may be of circular, square or rectangular cross-section. The illustrative circular form preferably is selected as having a diameter ranging between approximately 0.0001 and 0.0002 inches. The frequency of vibration and other related characteristics of tungsten, as well as of other potential candidate materials, are readily obtainable from reference data and appropriate mathematical formulae found in various mechanical engineering handbooks, such as Kent's Mechanical Engineer's Handbook, 11th Edition. It is understood that one available form of tungsten wire as a feasible diameter of 0.000128 inches, with good tensile strength (264,000-700,000 p.s.i.) and frequency of vibration factors, among others, for a contemplated preferred length ranging from approximately one to one and one-quarter inches. Other considered materials calculated out to diameters much too fine and weak, whereas for the selected tungsten wire diameter range, the tungsten wire proved less likely to sag or deflect under its own weight. Its good overall characteristics lend potential inherent ruggedness and durability to the device, with insignificant propensity to incur undesired actuation by normal activity movement of the wearer. Additionally, tungsten has quite acceptable electrical conductivity characteristics, and is a more readily available material which lends itself to existing manufacturing technology.

In constructive development of this device, three types of resonator reeds or beam formulae were considered:

(a) Cantilever—deflection of reeds of most materials under their own weight proved too great for practical use, although the selected tungsten material remains a possibility for use under laboratory controlled conditions for such a cantilever type reed.
  (b) Fixed ends beam—beam with sliding collar to vary the effective length as a means of varying the response frequency, lends itself to permit wearer to adjust his warning device to his own particular warning frequency.
  (c) Fixed ends beam—beam or reed of essentially fixed length, but subjected to slight selective variable reed tensioning to vary the frequency of response. Probably is the most satisfactory but would require laboratory type adjustment of the reed tension due to extremely fine adjustments required.

In use of a selected metal reed, the construction is such that its effective length can be varied by sliding a collar along its length to thereby adjust the frequency of response. The length and diameter of the reed is such as to allow resonant frequency range adjustment within the human heartbeat range of from approximately 60-200 cycles/minute. FIG. 16 is a graph which shows the exemplary effective length adjustment of the reed for various frequencies or heartbeats per minute.

Figure 17:
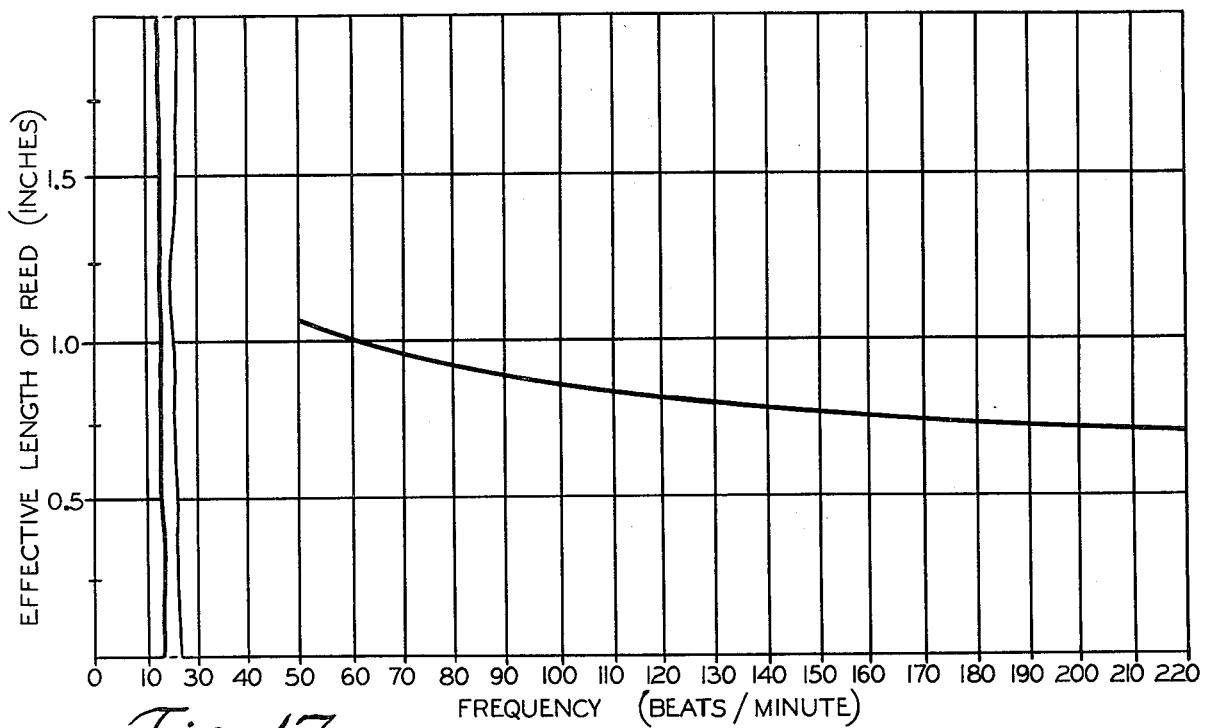
FIGS. 17 and 18 are graphs showing computed relationships first of the effective reed lengths and their corresponding natural frequencies, and secondly showing reed tension related to corresponding frequencies.

FIG. 17 is another graph showing an exemplary range of reed tension to achieve a corresponding desired range of frequencies or beats per minute, which is applicable to a modified embodiment depicted in FIGS. 8-15.

Proceeding with the embodiment of FIGS. 1-7, it is apparent that it relates to the aforementioned type (b), i.e. a beam or reed having fixed ends with a slidable collar. Thus, the tungsten wire resonator or reed R is of the aforedescribed character, and is suitably affixed to the case H closely parallel to the slot 18, conceivably with its opposite ends passing through oppositely aligned slotways or apertures 28, 28 (FIG. 3). Alternatively, in the case of a metallic housing case, the tungsten read may be soldered or brazed in place. Intermediate the reed ends, prior to affixing the reed into the casing apertures 28, 28, frequency response adjustment means are used in the form of a slidable collar subassembly 30. An exemplary collar assembly can be better seen in FIG. 5A. It includes a collar member 32 having an internally threaded stem portion 34 and a center through bore 36. Preferably, bore 36 is sized to provide a very close sliding fit with the reed R. It further includes a pointer knob 38 having a center bore to accommodate set screw 40 whose threaded shank cooperates with the internal threads in stem 34. FIG. 4 shows how the adjustable pointer knob cooperates with the pulse rate scale showing exemplary calibrations for a range of from 60–200 cycles or beats per minute. The scale is suitably imprinted upon surface 14 of the case H.

In the depicted form of FIGS. 3–5, the aforementioned electrical circuit C includes a portion of a conductor wire 42 which also spans the resonator chamber RC in closely parallel form to the reed R. Wire portion 42 is stretched between apertures 44 (FIG. 3), or a pair of suitable mounting slots generally similar to the slot 108, shown in the detail of FIG. 14, and in which case both wire 42 and reed R may be suitably affixed to case H. Other conductor wires may be contained within suitable recesses provided in the case or cover members, or the circuit may be comprised of some printed circuit form. It is apparent that upon pulse-induced vibration of the membrane/diaphragm D, the response frequency of reed R results in it ultimately making contact at essentially a midpoint are designated by circle 46 (FIG. 4) between the pointer knob's collar and the left side of case H through where wire 42 and reed R pass. Because of potential undesired contact by reed R with the conductor wire also on the right-hand side of knob 38 in FIG. 4, the reed wire R is provided on that side with a suitable form of combined vibration-damping-and-electrical-insulating means. This latter means may be in the form of a rubber or rubber-like resilient compound material disposed in a thread-like or spring-like form loosely spiraled around reed R, as shown at 48 (FIG. 4). Insulating thread 48 is attached to the collar and to the case H or to the end of reed R adjacent the case H, so as to enable it to stretch out and retract as needed depending upon the setting of knob 38 along the slot and pulse rate scale.

A removable cover assembly 50 including cover member 52 overlays surface 14 of the basic housing case H, and serves a dual purpose. One is to protect the adjustment knob/scale and the second is to support and enclose part of the electrical circuit C or components thereof; that is, more preferably it encloses at least part of the three facet signaling means (flasher/light 1, buzzer b, and vibrator v) in conjunction with the mode selector switch SS and release-reset switch RS. Cover 52 may be removably attached by friction catch (not shown) or by suitable fasteners 53 (FIG. 4). The cover 52 is further recessed internally at 55 (FIG. 5). This recessed portion in cooperation with the medial slot 18, complementally prevent undesirable damping of the harmonic oscillation of the reed.

Reference is now made to the electrical circuit C as schematically depicted in FIG. 6, in which it is also shown as generally related to a phantom line schematic representation of the casing H.

The resonator reed R is closely spaced in parallel to bare wire portion 42 of a conductor wire, both spanning the midportion of the resonator chamber RC, and coating to form a normally open switch of the circuit C. Continuing from wire portion 42, at the left hand side as seen in FIG. 6, a length of insulated conductor wire 54 is connected to positive terminal 54 of coil 58 of a double acting solenoid operated holding relay switch 60, as well as to one of the switch contacts 66a to be described hereinafter. The other terminal 62 of coil 58 is grounded, as shown at 64. The movable core thereof carries first switch-closing arm 66 and a second switch-closing arm 68 adapted to respectively close against first switch contacts 66a and second switch contacts 68a when energized via remaining circuit conductor wires and components as shown. A further conductor wire 70 interconnects terminal 72 of the resonator reed R with the positive side of a preferably miniature power source battery 74, with the negative terminal of said battery being grounded at 76. Located between terminal 72 and battery 74, a branch conductor wire 78 continues, via a series-connected normally closed release-and-reset switch RS, and connects with the respective right hand side contacts of the aforesaid switch contacts 66a and 68a.

Continuing relative to FIG. 6, the left hand switch contact 68a of relay 60 is connected with four further in-parallel arranged subcircuits via the selector switch SS, the latter of which is used to select the mode or modes of warning signals to be potentially activated by the device when in use. Selector switch arm 80 can be selectively moved to any of the contacts 1, b, or v to establish separate warning circuits respectively with a visual flasher light L, an audible buzzer B, or a sensory vibrator V. The sub-circuit for the visual signal includes the conductor wire 82, which after the in-series connection of the flasher unit 84 and light L is connected to a ground point 86. Similar sub-circuits for the buzzer B and vibrator V are denoted at 88 and 90 respectively. An additional contact A on the selector switch alternatively provides for potential simultaneous activation of all three signal devices via conductor wires 92, 94, 96. Appropriate diodes or other suitable equivalent devices, are used in each portion of these respectively different signal subcircuits to assure blockage of electrical current flow in a counter direction, thereby preventing electrical shorting out through any of these subcircuits when switch SS is in a position other than the A position. The A position will effect concurrent energization of all three of the signals. Alternative combinations of the circuits may be arranged as desired.

As briefly mentioned hereinabove, the case H or cover member 50 may be provided with appropriate recesses or channels 98 to accommodate the various circuitry wiring or other components. The aforedescribed circuitry may be fabricated alternatively, at least in part, to a form of printed circuitry for either of the exemplary embodiments being described herein.

OPERATION

Operation of the embodiment of FIGS. 1–7 is believed to be self-evident, but will be reviewed again. The warning device assembly A is mounted by suitable strap means so that the diaphragm D overlays a pulsating artery in a manner having the reed parallel to the artery. This is preferably at the underside of the wrist, although it could also overlay the heart directly, or be adapted for mounting at other areas of the anatomy where one's pulse can be readily detected. During the course of the wearer's activities, if the pulse rate reaches the prescribed maximum safe level, for example to 120 beats per minute to which the scale has been set in FIG. 4, the pulsing vibrations of the artery impact the case via the diaphragm. The vibrations are amplified in the resonator chamber causing the reed to resonate or vibrate at the natural harmonic frequency for the preset length, or tension as per second embodiment hereinafter. The vibrating reed ultimately makes contact with the adjacent electrical wire to close the circuit which in turn closed the switches of holding relay 60. Electrical current from the battery 74 locks and holds the relay closed, with the current then activating whichever mode of warning signal has been selected by the selector switch SS. The selected mode warning is then transmitted to the wearer and/or to his companions, so that the wearer or friends will take appropriate action to relieve the stressful situation, i.e. cease the working, slow down, lay down and rest, and avoid further physical or mental stress. To release or stop the warning signals, switch RS is opened which opens the relay switches. Switch RS is then reset to reprepare the device for operation once again in the same manner.

DESCRIPTION OF MODIFIED EMBODIMENT

Figure 18:
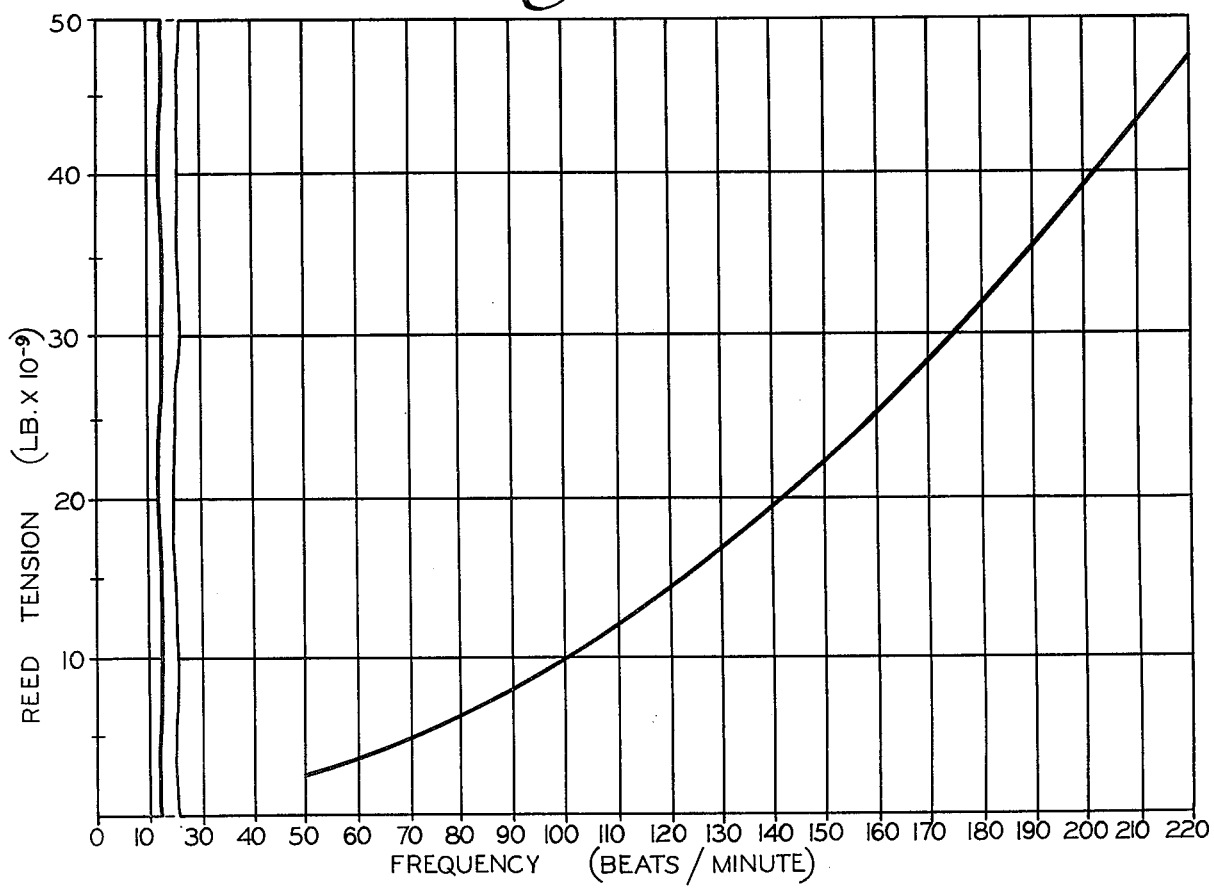

Referring next to the embodiment depicted in FIGS. 8-15, it includes a base case 100 having a resonator chamber RC' covered the same manner by diaphragm D', a similar transverse slot 102, and a suitable cover member 104 (FIG. 9), all basically the same as shown and discussed relative to FIGS. 3-5. A basically identical electrical circuit like that in FIG. 6, is to be used, including a conductor wires 42' and 54' (FIG. 14). In this embodiment, the metal reed R', while also held or fixed at both ends, is subjected to slight variable tensioning to vary its frequency of response. FIG. 18 is a graph representative of the calculated values for use with this embodiment.

Continuing, the reed R' is suitably anchored within the case so as to span the lower converging portion of the chamber. The left hand end portion may have an enlarged anchor head 106 to cooperate with one of a pair of end slots 108, 108. The other end is attached to the case by suitable tensioning means T, which may have a form as depicted in FIG. 11 or 15. Tensioning means T may comprise a male threaded tubular member 110 and a complementary female threaded collar member 112, respectively. The thread design is such that the coating tubular and collar members maintain any selected relative position to which they have been rotated, even under varying degrees of axial tension applied thereto.

This adjustment tensioning assembly T is provided with calibration markings similar to those on a micrometer. For example, a single reference mark 114 may be imprinted on the external surface of one of the members, preferably the threaded tubular member 110, and a plurality of circumferentially spaced gradation marks are imprinted upon an adjacent external surface of the other member, i.e. upon collar member 112. The gradation mark spacings will depend upon the desired various tensions to be applied to the reed. For example, with regard to an approximate one inch length reed to obtain acceptable operative increments of relative rotation necessary to impart corresponding requisite tension on the reed, calculations of the various ranges of frequency (cycles per second) have resulted in selecting increments of from about 20° to 22½° for each 10 pulses of the aforesaid 60-200 pulse gradation spacings. This may be achieved by use of screw threads having an approximate lead of one 360° turn per 0.01 inch of axial movement, or modified relative thereto as computations may require. In this regard, it is preferable that the selected screw may be chosen so that collar 112 rotates preferably not in excess of 360° in order to achieve the full selected range of tensioning between 60 and 200 cycles per minute. As shown herein, collar 112 would rotate approximately 315° to cover the aforesaid range.

The gradation marks are shown in FIGS. 12 and 13, with the apices 116 of the depicted knurlings constituting the gradations which are identified by their corresponding frequency/cycle indicia 130, 140, 159, etc. on the surface of the collar 112. FIG. 12 is an elevational detail view of the collar assembly tensioning means taken approximately on line 12—12 of FIG. 11.

Continuing with the description relative to FIG. 11, collar 112 is shown provided at its center portion with a tapered Teflon bearing insert 118 against which the swaged reed-anchoring collar 119 makes a low friction line contact via preferably its outer generally spherical surface. Anchor collar 119 also may be fabricated of Teflon to minimize friction between these co-acting parts, to reduce or eliminate imparting of axial twist to reed R' during tensioning adjustment of the reed. A shallow cap member or plug 111 (FIG. 11) is preferably used to close off any required access ports in the sides of the body case 100.

FIG. 15' is representative of a contemplated modification of reed anchor portion within the collar 112'. In this form, the Teflon bearing insert 120 is an annular disc seated in the recess 122. Cooperating with Teflon insert 120, via preferably 120° circumferentially spaced three-point contact buttons 124, is a preferably Teflon disc 126. Disc 126 may be held in place as shown by a similar anchor collar 119' which may also be suitably swaged onto the end of reed R'.

Concluding the description of FIGS. 11 and 14, the tensioning means assembly T is preferably maintained in a prerequisite position by help of annular shoulders at opposite ends cooperating with complemental recesses in the housing case. Similarly the anchor head 106 of reed R' may also be maintained in a desired prerequisite position by means of circumferentially spaced complemental boss-like projections 107 integrally formed on the case. The overall operation is deemed to be apparent from the foregoing detailed description, with the understanding that fine adjustment of axial tension on reed R' may better be achieved by more experienced lab technicians in accord with the desired pulse beat requirements, as determined in cooperation with the wearer's physician. FIG. 18 is a graphic correlation between reed tension and frequency.

Referring lastly to the embodiment shown in FIG. 16, there is shown a warning device assembly 130 comprising basically the same type housing case, with resonator in a resonator chamber covered by a membrane diaphragm on one side and a cover on the other side. Suitable strap means 132 are shown fragmentarily to facilitate mounting thereof on one's body, as needed. Instead of the casing assembly 130 housing the electrical circuit and related warning signal means, much of it is disposed within a small carrying case 134, which may be readily inserted into a shirt or jacket pocket, or also may be strapped to the wearer's body, as by strap means 136. While a selector switch arrangement similar to that shown in FIG. 6 may be used herein, an alternative thereto is to use a plurality of jack or plug and receptacle type connectors, designated on the lower part of case 134 by the same initials L (light), V (vibrator), B (buzzer) and A (all), for operative cooperation with plug 138 at one end of flexible conductor cable 140. A jack type connector 142 at the other end of cable 140 is used to connect the reed and conductor wires (corresponding to R and 42 located within assembly 130) with the rest of the circuit means housed within carrying case 134. Case 134 also contains the signal displays shown in the upper part thereof and correspondingly designated B, L, and V. A suitable reset switch or button RS is also designated thereon.

In use, it is obvious that when the carrying case 134 is chosen for carrying within a pocket of the wearer's clothing, the plug 138 would not be used in association with the receptacle designated L. The operation of the warning device is essentially the same as previously described.

While three exemplary operative forms of this invention have been specifically shown and described, it is understood that those skilled in the art may make some further variations and modifications, such as utilizing all electronic components in conjunction with a printed circuit arrangement, without departing from the inventive concept and scope disclosed herein and as defined in the appended claims.

What is claimed is:

1. A portable blood pulse rate monitor and stress warning device for warning of imminent heart trouble to the user of the device, said device comprising:

case means for housing components of the device, said case means including a case member having wall means defining a dual purpose combined resonator-amplifier chamber in the form of:
a shallow horn or hopper-shaped pulse-amplifying chamber having a closed-off large end and a smaller oppositely disposed narrowed and elongated open end;
a membrane stretched across and overlaying said latter chamber at its large end to close off same, said membrane adapted to lay against a given pulse area and to amplify the attendant pulse thereat;
a resonator in the form of a thin linear reed supported by and within said case member in a manner extending medially across said chamber adjacent said narrowed open end thereof;
said resonator reed being of a material characterized by natural sympathetic vibration capability having a predeterminable frequency of response when vibrating;
means for varying the frequency of response of said reed;
electric circuit means with operatively connected battery power means therefore, said circuit means comprising integrated warning alarm means and a circuit portion within said case member adapted to be energized by pulse-amplified resonator contact upon the attaining of a predetermined high level of resonator reed vibration or frequency response which corresponds to a predeterminable dangerously high level of pulse rate; and
said device having a variable range of pulse rates calibrated therewithin for selection according to different needs of different wearer's of said device.

2. The device of claim 1, wherein said resonator reed is a fine tungsten wire having a diameter ranging between approximately 0.0001 and 0.0002 inches.

3. The device of claim 2, wherein said resonator reed is of appoximately from one to one and one-quarter inches in length in initial installation.

4. The device of claim 1, wherein said variable range of pulse rates calibrated therewithin include calibration scale means in association with said means for varying said reed's frequency of response, so as to facilitate correlating predetermined different frequencies of response with predetermined corresponding heartbeat or pulse rates set forth on said calibration scale means.

5. The device of claim 1, wherein said case means has strap means connected thereto to facilitate appropriate mounting on a user's body.

6. The device of claim 1, wherein said means for adjusting said reed's frequency of response includes an adjustable collar member having a close sliding fit upon said linear reed.

7. The device of claim 1, wherein said means for adjusting the reed's frequency of response includes reed-tensioning means, to impart predetermined different tensions corresponding to predetermined different frequencies of response.

8. The device of claim 7, wherein said reed tensioning means includes two complementary screw threaded relatively rotatable members, with said reed having one of two end portions affixed to one side of said case member and the other end portion affixed to one of said relatively rotatable threaded members so as to be selectively tensioned by the interaction of said two relatively rotatable members.

9. The device of claim 7, further including calibrated scale means applied complementally to said relatively rotatable members in a manner to correlate predetermined frequencies of response to calibrated predetermined levels of heartbeat or pulse rate.

10. The device of claim 1, wherein said electric circuit alarms means includes separate types of visual, audio and sensory alarms with respective subcircuits for each type thereof, as well as for concurrent operation of a collective plurality of said alarms; and selector switch means for effecting selective operation of individual alarms and for collective operation of a plurality of said alarms.

11. The device of claim 1, wherein all defined components constitute a unitary assembly having a relatively small overall size adaptable to be worn on a wearer's wrist, and further including strap means to facilitate removable attachment to and from the wrist.

12. The device of claim 1, wherein the defined resonator and case means constitute one basic subassembly, which also has strap means to removably attach to a wearer's body; further wherein said electric circuit with related battery power means and warning alarm means constitute another separate basic subassembly adaptable for carrying within a user's clothing and upon the wearer's body; and flexible wire conductor means adapted to operatively interconnect the aforesaid two basic subassemblies.

* * * * *

UNITED STATES PATENT AND TRADEMARK OFFICE
CERTIFICATE OF CORRECTION

PATENT NO. : 4,459,992
DATED : 15 November 1982
INVENTOR(S) : Marion V. Gwyn

It is certified that error appears in the above—identified patent and that said Letters Patent is hereby corrected as shown below:

Column 7, line 52, "coating" should be --"co-acting"--.

Signed and Sealed this

Twenty-sixth Day of February 1985

[SEAL]

Attest:

DONALD J. QUIGG

Attesting Officer     Acting Commissioner of Patents and Trademarks